United States Patent [19]
Bark et al.

[11] Patent Number: 5,972,002
[45] Date of Patent: Oct. 26, 1999

[54] APPARATUS AND METHOD FOR SURGICAL LIGATION

[75] Inventors: Jeff Bark, Burlington, Wis.; Frank D'Amelio, Buellton, Calif.; Richard Muller, Bronx, N.Y.

[73] Assignee: Cabot Technology Corporation, Santa Barbara, Calif.

[21] Appl. No.: 09/089,197

[22] Filed: Jun. 2, 1998

[51] Int. Cl.[6] ................................................. A61B 17/04
[52] U.S. Cl. ............................................ 606/140; 606/141
[58] Field of Search ................................... 606/140, 141

[56] References Cited

U.S. PATENT DOCUMENTS

| | | | |
|---|---|---|---|
| 2,131,924 | 10/1938 | Wappler | 606/140 |
| 2,541,542 | 2/1951 | Perez et al. | 606/140 |
| 3,687,138 | 8/1972 | Jarvik | 606/140 |
| 3,834,392 | 9/1974 | Lampman et al. | 606/140 |
| 3,870,048 | 3/1975 | Yoon | 606/140 |
| 3,911,923 | 10/1975 | Yoon | 606/140 |
| 3,934,589 | 1/1976 | Zimmer | 606/140 |
| 3,967,625 | 7/1976 | Yoon | 606/140 |
| 3,989,049 | 11/1976 | Yoon | 606/140 |
| 4,085,743 | 4/1978 | Yoon | 606/140 |
| 4,103,680 | 8/1978 | Yoon | 606/140 |
| 4,226,239 | 10/1980 | Polk et al. | 606/140 |
| 4,230,116 | 10/1980 | Watson | 606/140 |

FOREIGN PATENT DOCUMENTS

| | | | |
|---|---|---|---|
| 716726 | 5/1931 | France | 606/140 |
| 934257 | 9/1946 | France | 606/140 |
| 1561218 | 12/1967 | France | 606/140 |

OTHER PUBLICATIONS

1997 Circon Product Catalog, copyright 1996. p. GY–34.

*Primary Examiner*—Gary Jackson
*Attorney, Agent, or Firm*—Bradley M. Ganz

[57] ABSTRACT

A medical instrument for ligation of tissue and anatomical structures, including fallopian tubes comprises at least two slideable shafts concentrically disposed relative to each other. A first shaft has a tissue receiving recess into which tissue is retracted by a grasper. The grasper is disposed on the end of a second shaft that is extendible from the first shaft. A ring retainer on the second or a third shaft can hold one or more elastic rings that are displaceable by the instrument around tissue extending from the tissue receiving recess. The rings are held on a tapered or necked down part of the instrument so that the rings contribute little or nothing to the largest outer diameter (OD) of the portion of the instrument that is inserted into a patient's body. Because the ring or rings do not contribute to the OD of the instrument, the instrument may be constructed to fit within insertion channels of 5 mm or less.

31 Claims, 8 Drawing Sheets

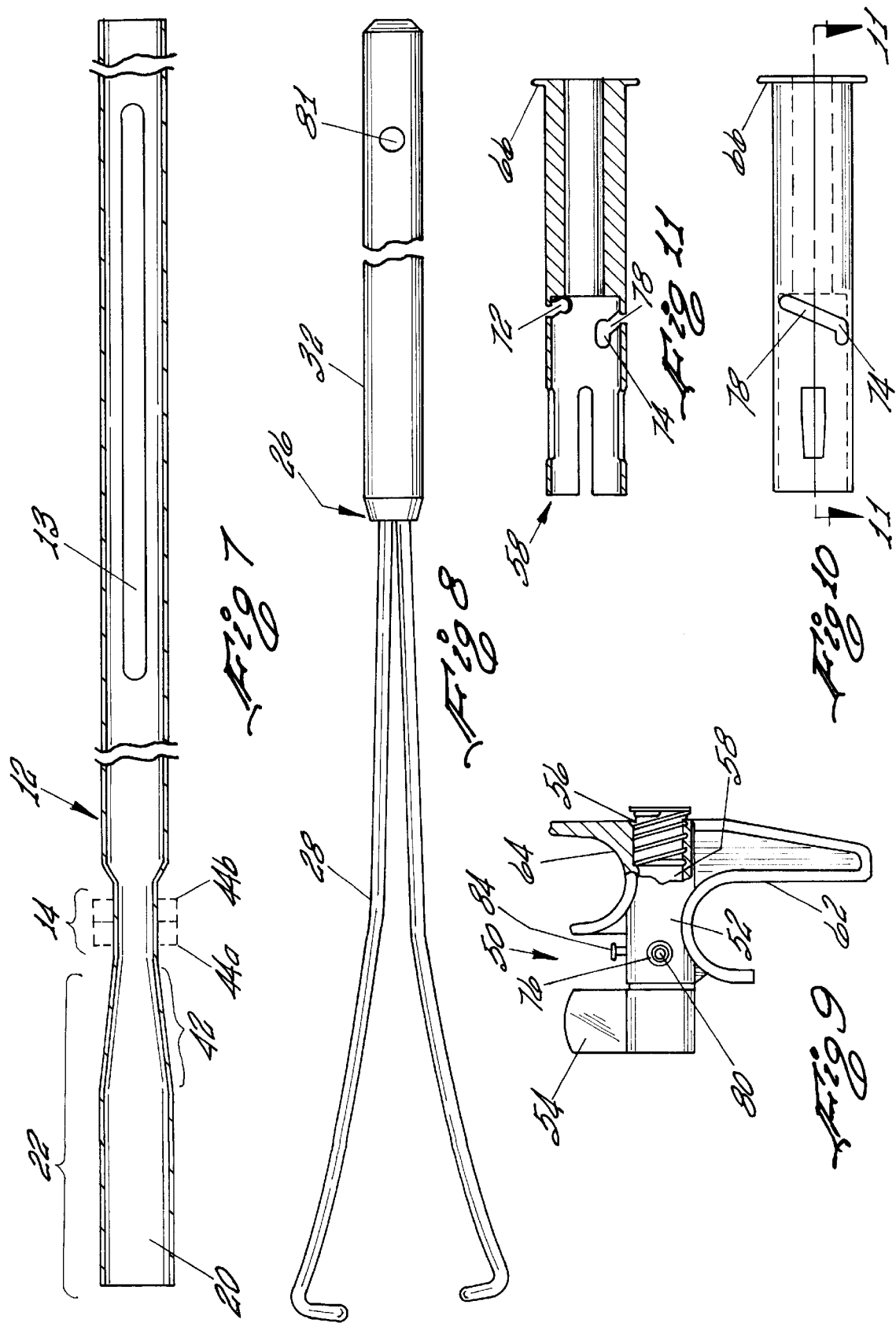

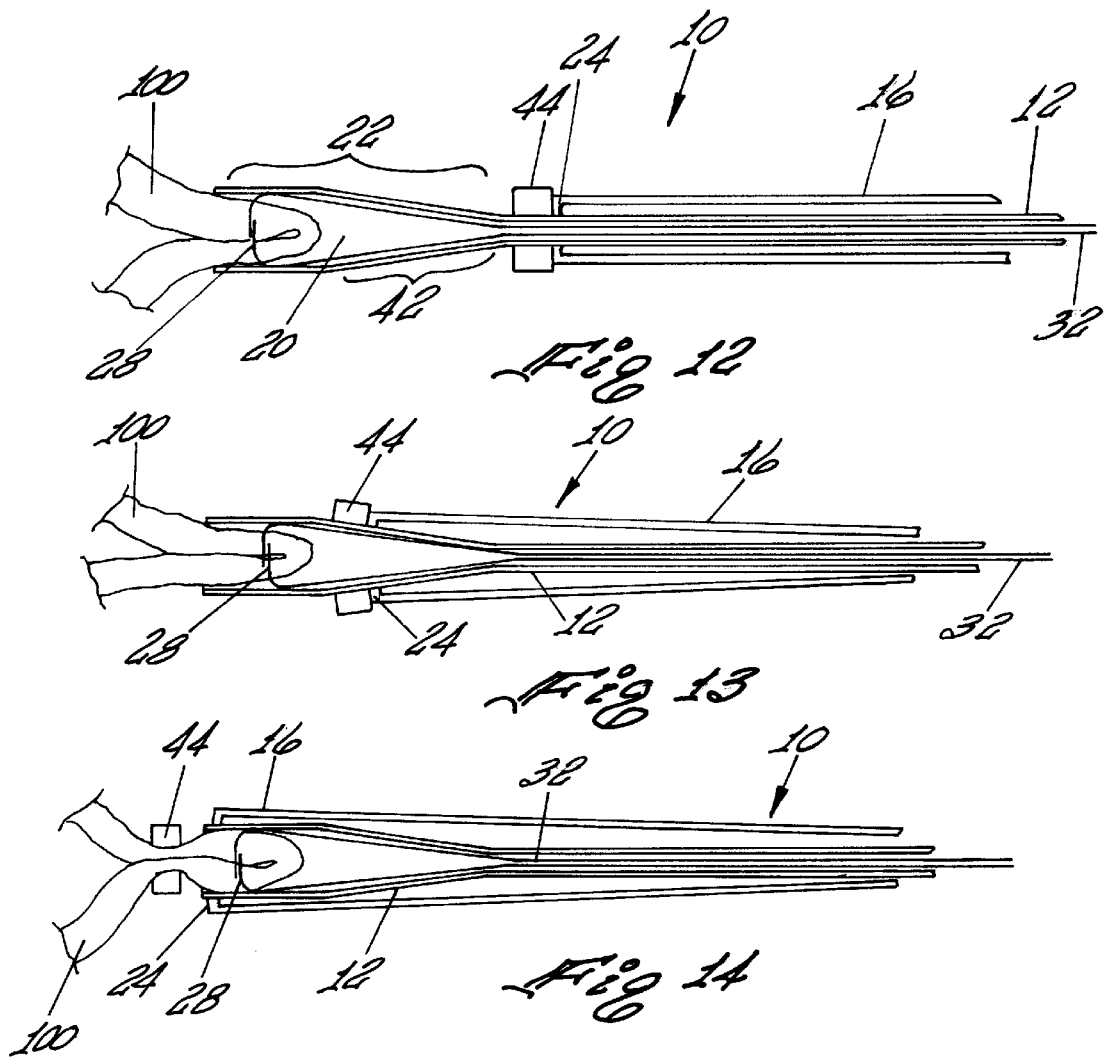
Fig 12
Fig 13
Fig 14
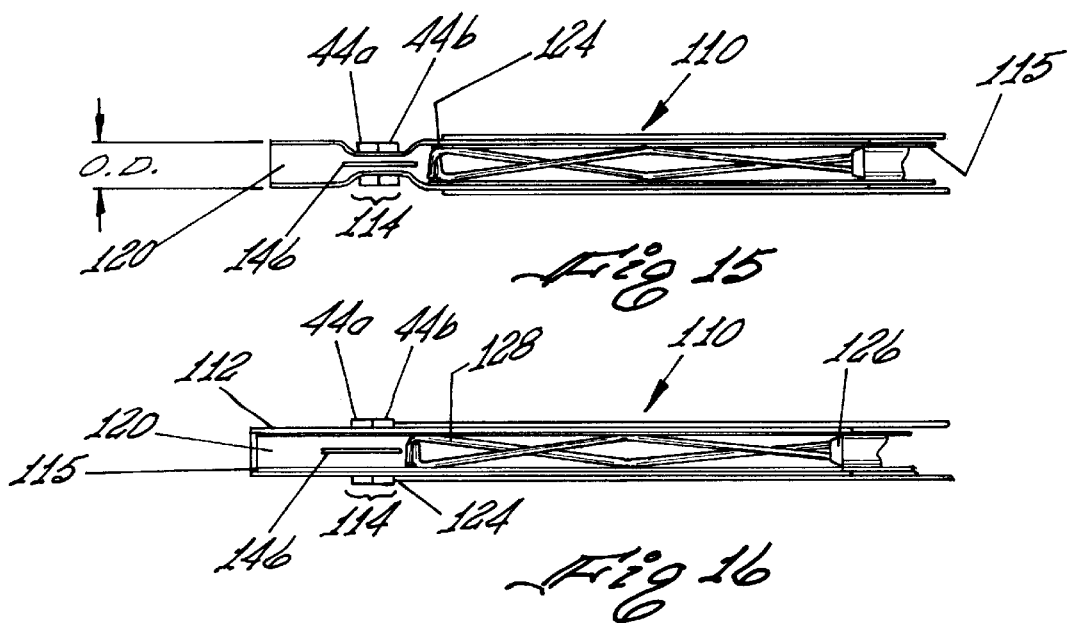
Fig 15
Fig 16

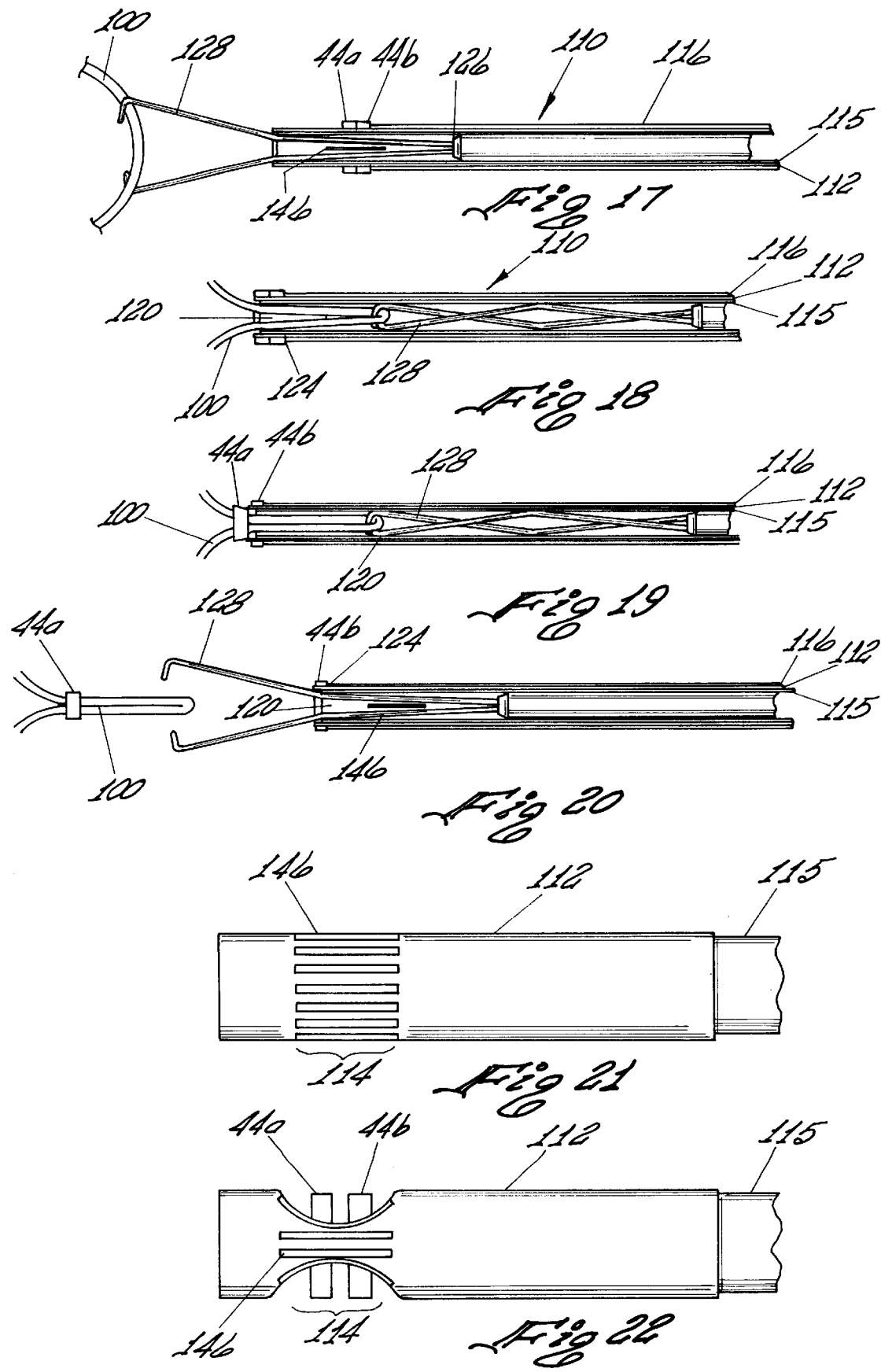

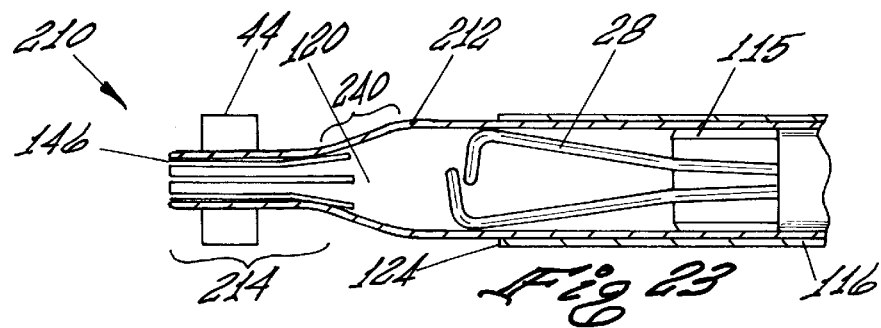
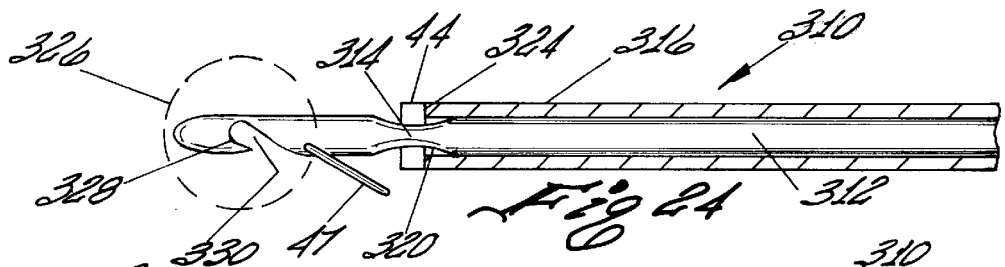
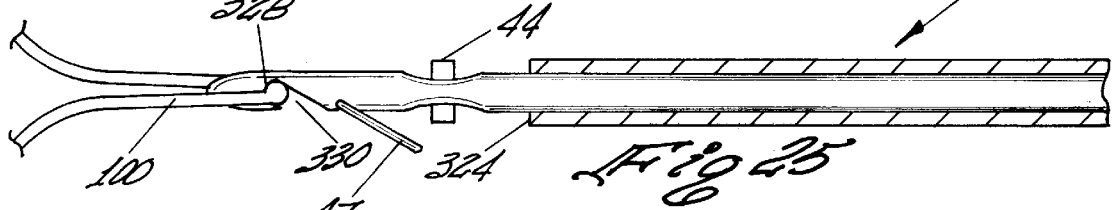
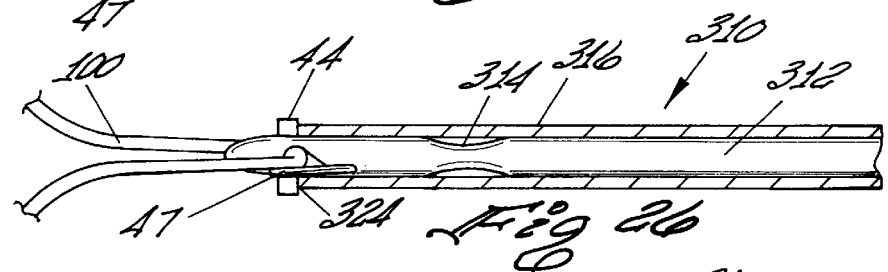
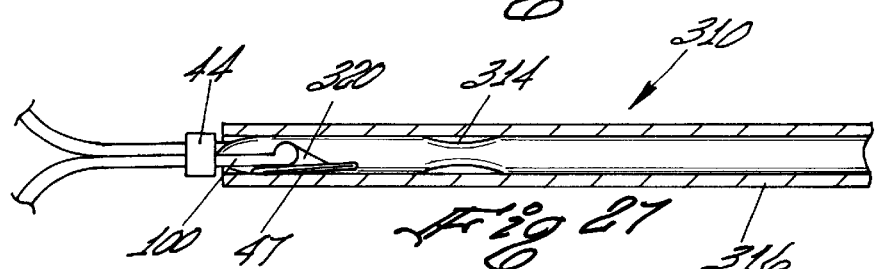
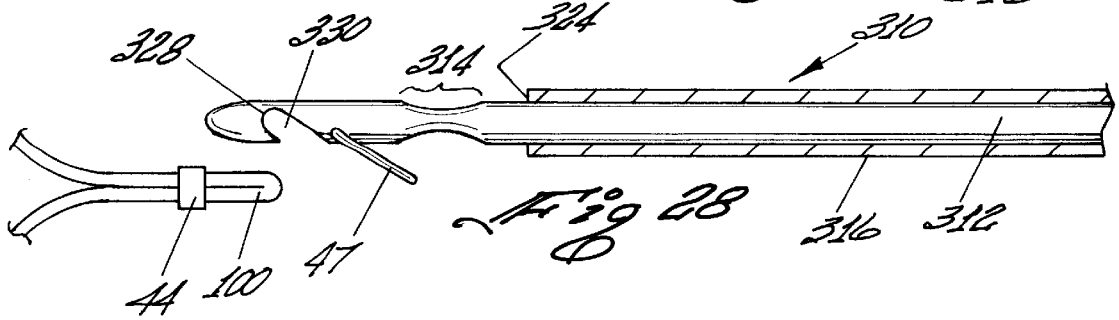

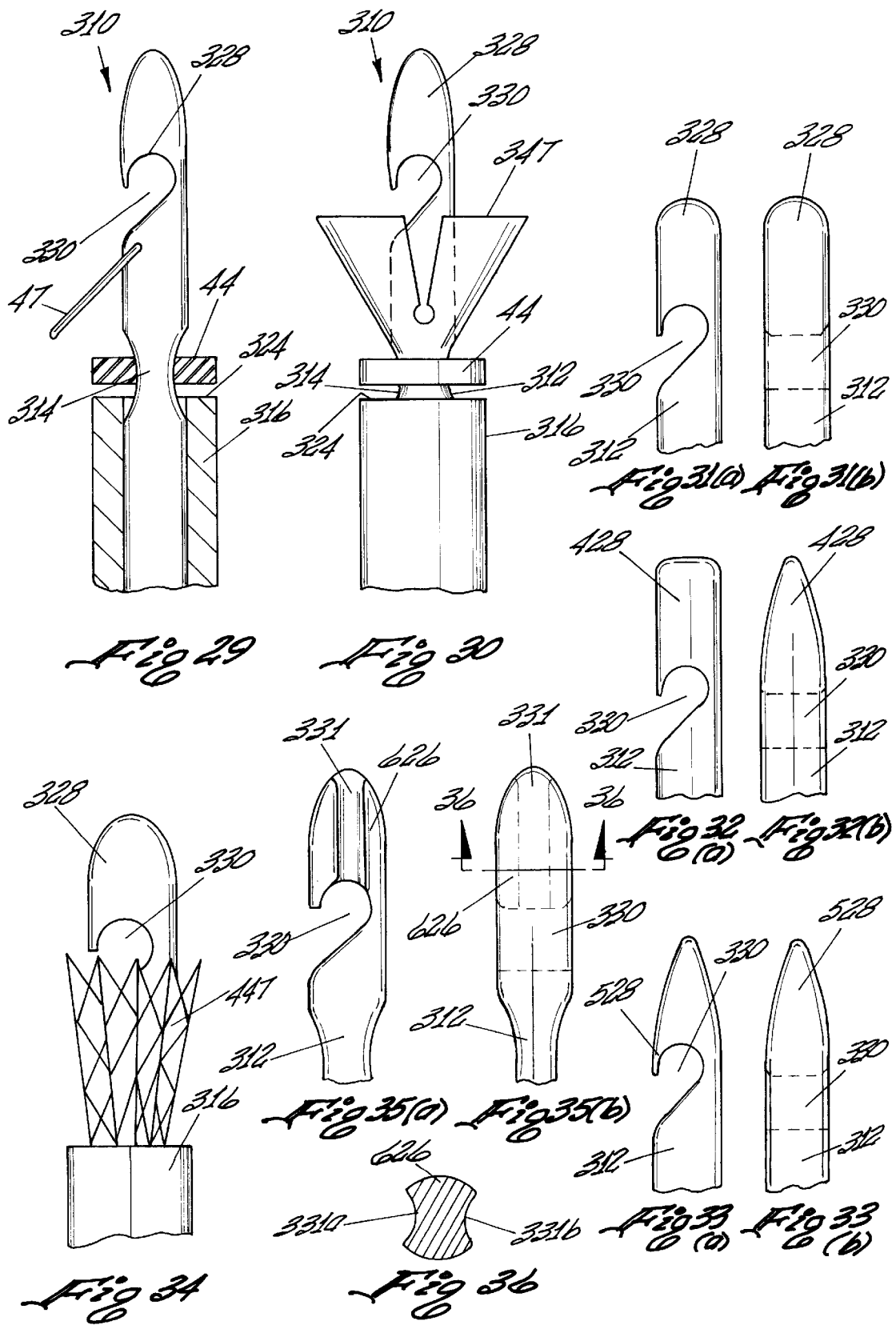

APPARATUS AND METHOD FOR SURGICAL LIGATION

BACKGROUND OF THE INVENTION

This invention generally relates to an instrument and method for surgical ligation of anatomical structures within a human or animal body. In particular, the instrument relates to ligation of reproductive tubes in the female or male anatomy to effect sterilization. The instrument places one or more elastomeric rings around the desired anatomical structure to bind, sever, or occlude the structure.

For example, under certain circumstances, a surgeon may need to sever or occlude the fallopian tubes of a female patient. The fallopian tubes may be severed according to various known procedures, including ligation through suturing the tubes, electrosurgical cauterization, and occlusion through a clip. These procedures are not satisfactory because they involve significant risk of infection or unintended damage to tissue, and they suffer from certain other disadvantages, as well. For example, a clip procedure may dislodge from the tubes with time. With electrosurgical sterilization, it is well-documented in the literature that unintentional burns can be inflicted on other organs, such as the bowel. Other procedures may require multiple entries of a surgical instrument through an incision, compounding the risk of infection or injury to the patient, and making the procedure unnecessarily complicated.

Because of these and other problems, ring applicator devices were developed that are inserted through channels on the order of ten millimeters in diameter. These devices have an inner cylinder slideably disposed in an outer cylinder. Grasping means are slideably disposed in the inner cylinder. The grasping means retracts a section of fallopian tube into the opening at the distal end of the inner cylinder. An elastic ring that has been placed circumferentially over the end of the inner cylinder is pushed by the outer cylinder off the inner cylinder and over the fallopian tissue extending from the opening in the inner cylinder's distal end. The ring binds around the tissue creating a u-shaped knuckle. A tightly fitted ring cuts off blood flow to the knuckle causing necrosis of the knuckle section of the tissue. This results in a sectioning of the tube, rendering the patient sterile. U.S. Pat. No. 4,085,743 to Yoon and U.S. Pat. No. 4,226,239 to Polk et al describe certain devices that deliver rings in the foregoing procedure.

Ideally, the devices used in minimally invasive surgical procedures should be insertable through the smallest possible incision. Devices are known that can be accommodated through eight-millimeter insertion channels. However, current demand is for medical instruments that may be inserted through even smaller channels. Smaller channels reduce the risk of infection and injury to anatomical structure, allow more precise surgery, and minimize trauma and scarring. The current demand in the surgical art is for surgical instruments that can be passed through insertion channels of five millimeters or less—as trends continue. Unfortunately, the known ligation instruments have not yet been adapted to fit or perform adequately in channels of about this size.

Simply scaling down existing devices does not solve the problem: the minimum size of the channel through which existing devices can be inserted first depends on the minimum cylinder diameter needed to accommodate the bulk size of the tissue to be retracted. The outer diameter of the outermost cylinder is added to this plus the outer diameter of the elastic ring that extends beyond the outer diameter of the outermost cylinder.

For example, the outer diameter of the straight-shaft cylinders used in prior art devices such as shown in U.S. Pat. No. 4,226,239 patent is generally about 6–8 mm. When the extending outer diameter of an elastic ring placed on the device is added to this, an insertion channel of at least about 8 mm is required. For these reasons and others, prior art devices have not been adapted to fit or perform adequately within channels approaching 5 mm or less.

The prior art devices also generally require at least three or more shafts concentrically and slideably disposed relative to each other. Under some circumstances, it is desirable to reduce the number of parts. This might hold true, for example, from the standpoint of manufacturing a low-cost, disposable device.

Existing devices also do not adequately address the problem of too forceful retraction of tissue into the relatively narrow recess of the instrument. Overly forceful retraction can damage sections of tissue unnecessarily. For example, if the damage to Fallopian tissue is severe enough, complications may arise, such as bleeding, scarring, and infection, which sometimes require re-surgery. The damage may also make reversal of the sterilization procedure impossible, foreclosing an important option to the patient. Accordingly, there is a need for instruments that reduce the risk of unintended damage to tissue being retracted.

SUMMARY OF THE INVENTION

This invention is an instrument and method for ligation of tissue or other anatomical structure. The invention can be passed through insertion channels at least as small as 5 mm. The insertion channel may be an aperture or passageway through tissue. Alternatively, it could be a channel formed in, or defined by, another instrument, such as an endoscope, cannula, or similar structure. For convenience, the use of the term "tissue" hereinafter is intended to encompass any other ligatable anatomical structures. While this specification generally speaks in terms of fallopian tubes, its teachings and principles carry over to the ligation of other kinds of tissue or structures.

One embodiment of this invention carries elastomeric rings around a tapered outer portion of the instrument that does not overlie the tissue receiving recess of the instrument. Because they are disposed in a tapered area, the rings contribute little or nothing to the largest outer diameter of the instrument. Therefore, the insertion channel may be of a reduced diameter. Another embodiment of the invention may be constructed from only two concentrically slideable shafts. A two-shaft construction results in small outer diameters and is simpler and less expensive to construct and use. These designs overcome the limitations prior art devices have in not being insertable through smaller insertion channel sizes.

More particularly, the present invention is an instrument for ligation of tissue that has a first shaft having a distal portion and a proximal portion. A second shaft is slideably disposed in the first shaft. A tissue receiving recess is disposed at the distal end of the instrument. The tissue receiving recess may be disposed in the distal end of the first shaft or the second shaft. A grasper for grasping tissue is slideably disposed in the first shaft and adapted to retract tissue into the tissue receiving recess.

The second shaft includes a ring retainer for receiving at least one elastic ring. The ring retainer comprises a distal segment of the second shaft, and the ring retainer has a reduced diameter relative to an adjacent second segment of that shaft. A displacement member is disposed on the distal end of the first shaft for pushing a ring off the ring retainer and around tissue extending from the tissue receiving recess.

Preferably, the ring retainer or the distal portion of the first shaft is expandable radially. The expansion allows the slideable displacement member disposed on the distal end of the first shaft to push a ring off the ring retainer and around tissue extending from the tissue receiving recess. In the case where the ring retainer is expandable, the instrument may further comprise an inner tube slideably disposed in the second shaft for expanding the ring retainer. In one embodiment where the distal portion of the first shaft is expandable, the distal portion of the second comprises a flared region of greater diameter than the distal portion of the first shaft. The distal portion of the first shaft expands as the flared region of the second shaft is pulled therein. In this embodiment, the tissue receiving recess is disposed in the flared region of the second shaft, with the ring retainer being disposed on the second shaft, proximal to the flared region.

The expandable shaft segment comprising the ring retainer or the distal portion of the first shaft may include one or more reliefs to facilitate the expansion. These reliefs may be in the form of slots, for example. Alternatively, the expandability can be provided by selecting shaft materials capable of expanding.

In the foregoing embodiments, the displacement member may comprise the distal end of the first shaft. Preferably, the displacement member provides a blunted surface for contacting the ring. In the foregoing embodiments, the grasper may be slideably disposed in the second shaft or it may be attached to the distal end of the second shaft, for example.

In other embodiments, the distal end of the second shaft includes a hook-like notch to capture and retract tissue within the tissue receiving recess. Accordingly, the distal end of the second shaft is the grasper in such embodiments. The ring retainer is located on a portion of the second shaft proximal the notch. To keep the tissue from falling out of the notch during retraction, a latching mechanism may be provided that closes over the notch as tissue is retracted into the tissue receiving recess. The distal end of the second shaft may also be adapted to perform additional functions such as the cutting or piercing of tissue.

In one particular embodiment of the invention, the instrument for ligation of tissue includes:

an outer shaft having a distal portion and a proximal portion;

an inner shaft slideably disposed in the outer shaft;

a tissue receiving recess at the distal end of the inner shaft;

a grasper slideably disposed in the inner shaft and adapted to extend from the instrument to grasp and retract tissue into the tissue receiving recess;

a ring retainer for receiving at least one elastic ring, the ring retainer comprising a first distal segment of the inner shaft, the ring retainer having reduced diameter relative to an adjacent second more distal second segment of the inner shaft;

the outer shaft being adapted to expand to receive the second segment of the inner shaft; and a displacement member disposed on the distal end of the outer shaft for pushing a ring off the ring retainer and around tissue extending from the tissue receiving recess.

In another particular embodiment, the instrument for ligation of tissue includes:

an outer shaft having a distal portion and a proximal portion;

an intermediate shaft slideably disposed in the outer shaft;

a tissue receiving recess at the distal end of the intermediate shaft;

a grasper slideably disposed in the inner shaft adapted to extend from the instrument to grasp and retract tissue into the tissue receiving recess;

a ring retainer for receiving at least one elastic ring, the ring retainer comprising a distal segment of the intermediate shaft having reduced diameter relative to an adjacent distal segment of the intermediate shaft, the ring retainer being radially expandable;

an inner shaft slideably disposed in the intermediate shaft for expandably engaging the ring retainer; and a displacement member disposed on the distal end of the outer shaft for pushing a ring off the ring retainer and around tissue extending from the tissue receiving recess.

In a further embodiment of the invention, an instrument for ligation of tissue includes:

an outer shaft having a distal portion and a proximal portion;

an inner shaft slideably disposed in the outer shaft;

a tissue receiving recess at the distal end of the outer shaft;

a grasper slideably disposed on the end of the inner shaft and adapted to extend from the instrument to grasp and retract tissue into the tissue receiving recess;

a ring retainer for receiving at least one elastic ring, the ring retainer comprising a first distal segment of the inner shaft, the ring retainer disposed adjacent a second more distal second segment of the inner shaft, the second segment comprising the grasper; and a displacement member disposed on the distal end of the outer shaft for pushing a ring off the ring retainer and around tissue extending from the tissue receiving recess.

The instrument may further include a safety linkage disposed on the grasper for preventing overly forceful retraction of tissue into the tissue receiving recess. It may also include a means to lock shafts of the instrument relative to each other to facilitate the loading of an elastic ring on the instrument.

The foregoing embodiments and features, and additional embodiments and features, are described in more detail below and in the attached drawings.

BRIEF DESCRIPTION OF THE DRAWINGS

FIG. 5 is a side view of an outer shaft of the embodiment of the present invention shown in FIGS. 1 and 2.

FIG. 6 is a front view of the distal end of the outer shaft of FIG. 5.

FIG. 7 is a side view of an inner shaft of the embodiment of the present invention shown in FIGS. 1 and 2.

FIG. 8 is a side view of a grasping assembly of the embodiment of the present invention shown in FIGS. 1 and 2.

FIG. 9 is a partial side section view of an actuator assembly of the present invention.

FIG. 10 is a side section view of a component of the actuator assembly of FIG. 9.

FIG. 11 is a section view of the component of FIG. 10 taken along line 11—11.

FIG. 12 shows a distal portion of ligation instrument of FIG. 1 with tissue retracted into a tissue receiving recess at the distal end of the instrument.

FIG. 13 shows the ligation instrument of FIG. 12 as a displacement member at the distal end of the outer shaft is pushing a ring off the instrument.

FIG. 14 shows the ligation instrument of FIG. 13 after the displacement member has pushed the ring completely off the instrument and around tissue extending from the tissue receiving recess.

FIG. 15 shows a side section view of an alternative embodiment of a ligation instrument according to the present invention that includes an expandable ring retainer.

FIG. 16 shows the embodiment of FIG. 15 after the ring retainer has been expanded by a slideable inner tube.

FIG. 17 shows the embodiment of FIG. 16 as the grasper is extended from the distal end of the instrument to grasp tissue.

FIG. 18 shows the ligation instrument of FIG. 17 after tissue has been retracted into a tissue receiving recess at the distal end of the instrument.

FIG. 19 shows the ligation instrument of FIG. 18 as a displacement member at the distal end of the outer shaft is pushing a ring off the instrument.

FIG. 20 shows the ligation instrument of FIG. 19 after the displacement member has pushed the ring completely off the instrument and around tissue that extended from the tissue receiving recess.

FIG. 21 is a side view of one embodiment of an expandable ring retainer on a section of a shaft component according to the present invention.

FIG. 22 is a side view of the ring retainer of FIG. 21 with two elastic rings disposed thereon.

FIG. 23 is a side section view of an alternative embodiment of an expandable ring retainer according to the present invention.

FIG. 24 is an alternative embodiment of a ligation instrument of the present invention that includes a notch and latch mechanism.

FIG. 25 shows the ligation instrument of FIG. 24 grasping tissue for retraction into the tissue receiving recess of the instrument.

FIG. 26 shows the ligation instrument of FIG. 25 as tissue is retracted into the instrument, and as a displacement member is pushing a ring off the instrument.

FIG. 27 shows the ligation instrument of FIG. 26 after the ring has been pushed off the instrument and around tissue extending from the tissue receiving recess.

FIG. 28 shows the release of the tissue from the instrument of FIG. 27.

FIG. 29 is a side section view of the distal portion of the instrument of FIG. 24.

FIG. 30 is an alternative embodiment of a latching mechanism for the instrument of FIG. 24.

FIGS. 31(a) & (b) are different perspectives of an alternative embodiment of the distal portion shown in FIG. 29.

FIGS. 32(a) & (b) are different perspectives of an alternative embodiment of the distal portion shown in FIG. 29.

FIGS. 33(a) & (b) are different perspectives of an alternative embodiment of the distal portion shown in FIG. 29.

FIG. 34 is an alternative embodiment of a latching mechanism for the instrument of FIG. 29.

FIG. 35(a) & (b) are different perspectives of an alternative embodiment of the distal portion shown in FIG. 29.

FIG. 36 is a section view of taken along line 36—36 in FIG. 35(b).

DETAILED DESCRIPTION OF THE INVENTION

Figure 1:
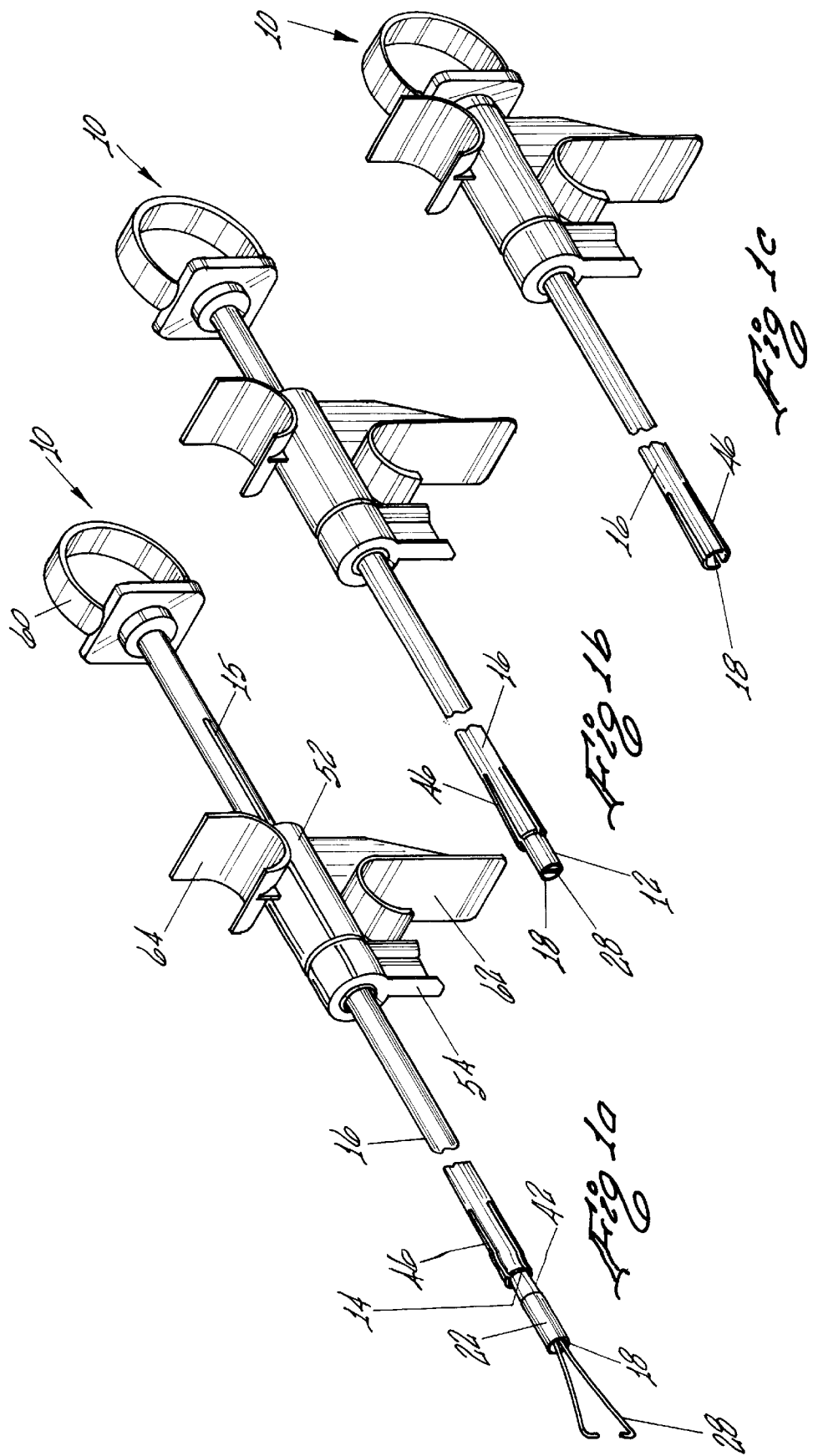
FIG. 1a–1c show perspective views of a ligation instrument of the present invention in different operational positions.
Figure 2:
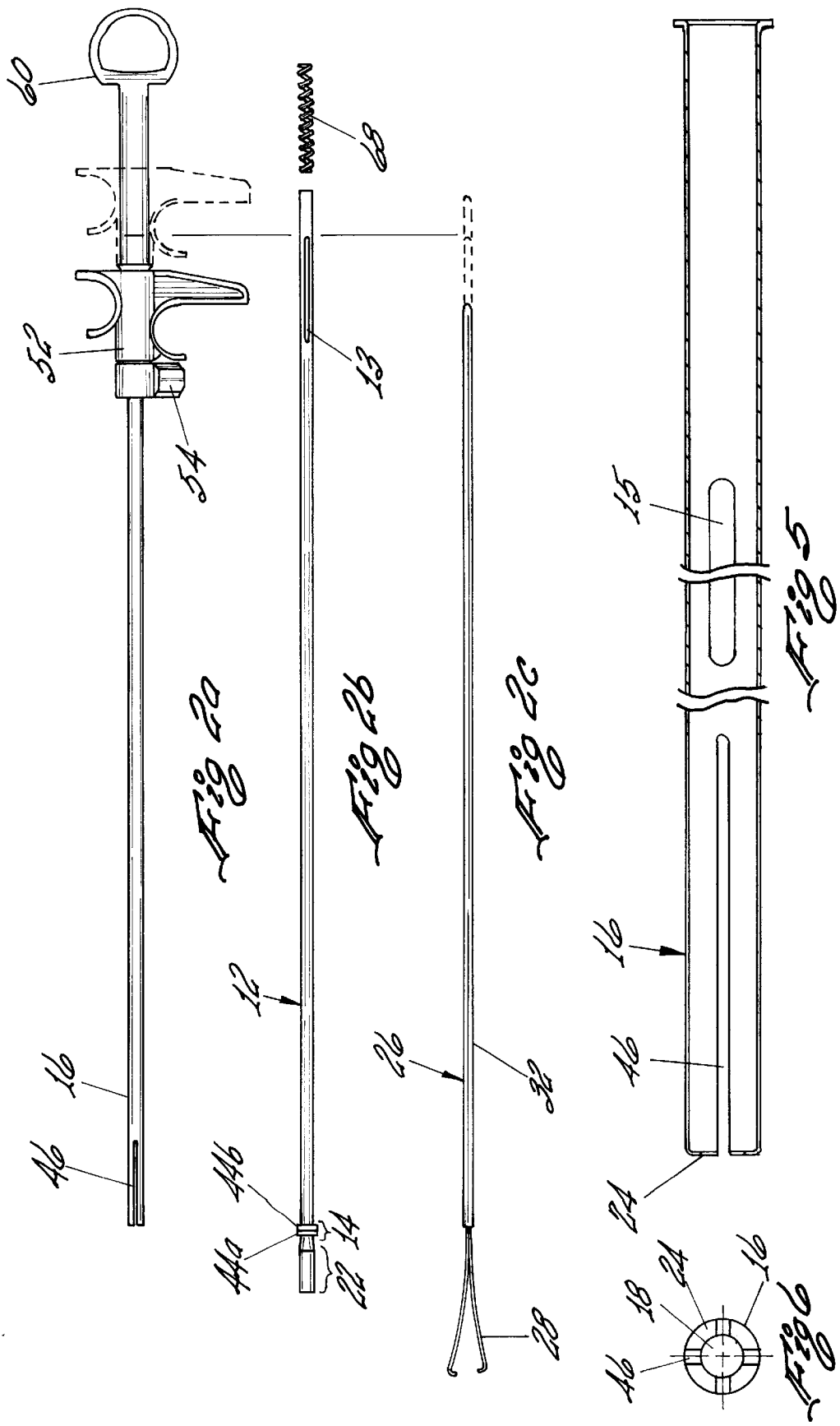
FIG. 2a–2c show an assembly view of the ligation instrument of FIG. 1.

The present invention is an instrument that delivers elastomeric rings around tissue to sever, bind, or occlude the tissue. The instrument includes a tubular recess into which tissue can be retracted; grasping means for retracting the tissue into the recess; an elastic ring retainer for holding one or more rings; a means to displace an elastic ring around tissue extending from the recess; and an actuator for moving the parts of the instrument relative to each other.

Turning to the FIGS. 1–14, instrument 10 includes a first elongate shaft 12 having a proximal portion and a distal portion. Shaft 12 is slideably disposed in a second tubular outer shaft 16. A distal portion of shaft 12 may be extended or retracted from a distal opening 18 at the distal end of outer shaft 16. The extendible portion of shaft 12 includes an area of increased outer diameter 22 relative to the proximal portion of the shaft. In instrument 10, this area of increased outer diameter comprises a flared or generally funnel-shaped region 22, which is distal to a proximal tapered region 14. The flared region 22 includes section 42, which increases in diameter moving in a distal direction from region 14.

Tapered region 14 serves as a retainer for holding at least one elastomeric ring 44. Ring 44 may be stretched over the distal end of the instrument to circumferentially place it on ring retainer 14. The instrument 10 is used to deliver ring 44 around tissue 100 to ligate the tissue, as described in more detail below. Elastic ring retainer 14 may be constructed to hold multiple rings 44a and 44b for sequential release of the rings over tissue. In instrument 10, the length of ring retainer 14 should be at least the width of ring 44 or the width of a multiple number of rings disposed on the ring retainer.

The inner shaft 12 is flared shaped at its distal end, tapering in the proximal direction. By disposing a ring on ring retainer 14 in the tapered region, a ring's thickness contributes little or nothing to the largest OD of the instrument. Thereby the tapered region/ring retainer 14 of the present invention overcomes the drawback in prior art of the loaded ring contributing to the largest insertable OD of instrument 10, as labeled in FIG. 7.

Instrument 10 includes a recess 20 at its distal end located within the distal portion of shaft 12. Recess 20 is the portion of the instrument into which a desired length of tissue can be retracted. In the case of instrument 10, recess 20 is disposed in a distal end region of shaft 12, and is defined by the inner surface of flared region 22. In other embodiments, such as the one shown in FIGS. 24–28, recess 20 may be defined by another cylinder such as the outer cylinder 316. The diameter of the recess depends on the nature and thickness of the material to be retracted. The length of the recess depends on the length of tissue to be bound into a knuckle.

Grasping assembly 26 is slideably disposed in shaft 12 for retracting tissue 100 into recess 20. The Grasping assembly 26 comprises grasper 28 and a connecting rod 32. Grasper 28 may comprise any number of grasping implements known to those skilled in the art. As shown in FIG. 8, grasping assembly 28 may be embodied as a forceps having arms of a spring metal. The arms are biased in an open position. Grasping member 28 is moveable between a position extending from the end of shaft 12 to a position in shaft 12 proximal recess 20. In the extended position, the grasper 28 is positioned so that tissue 100 is disposed between the arms. As the grasper is retracted into shaft 12, the biased arms engage the opening of shaft 12 causing the grasper's arms to converge on tissue 100 and retract it into recess 20. The rings may be placed at different locations on a length of tissue by repositioning the grasper 28.

Generally, fallopian tubes range in diameter from about 1 to about 5 millimeters. The tissue receiving recess in an instrument for ligation of fallopian tubes typically may be about 5 to 15 millimeters long with an inner diameter of about 1 to about 5 millimeters.

Figure 4:
FIG. 4 shows an alternative embodiment of a shaft of the present invention that includes a safety linkage in the form of magnetic pairs.

Grasper 28 is disposed at the distal end of a connecting rod 32. Connecting rod 32 is preferably rigid to allow the advancement of forceps from the opening of inner shaft 12 and the retraction of the forceps back into shaft 12. Connecting rod 32 is preferably made from stainless steel or a thermal plastic that will withstand cleaning and sterilization by normally accepted medical methods. A grasper 28 in the form of forceps may be made from stainless steel full-round wire. Other materials may be used as long as they meet the functional requirements of the forceps. In addition, to help minimize the instruments OD, wire with a half-round or other cross-section configuration may also be used. The forceps wires may be bent at an angle or fashioned with a radius to bias them to open when they are extended out of shaft 12. A radiused profile of about 30°, as shown in FIGS. 4 and 8, is advantageous for smoother retraction of the forceps into shaft 12. The forceps wires can be attached to the connecting rod by brazing, gluing or any other suitable joining means known to those skilled in the art.

The displacement of an elastomeric ring over tissue by ligation instrument 10 is illustrated in FIGS. 12 to 14. Grasper 28 is advanced from the end of the instrument by distally extending grasping assembly 26 from the distal end of shaft 12 to grasp tissue. In the figures, the tissue is a fallopian tube. The grasping assembly 26 is retracted to draw a portion of tissue into recess 20. With the tissue grasped within recess 20, the extended portion of shaft 12 is then slid proximally relative to the distal end of shaft 16. As this occurs, displacement member 24 begins to urge elastic ring 44 distally along shaft 12. In the embodiment shown, displacement member 24 comprises the distal end of shaft 12.

As the displacement member begins to urge ring 44 forward, flared region 22 of shaft 12 begins to enter the distal opening of shaft 16. To accommodate the larger diameter of the flared region 22, the distal portion of shaft 16 is expandable. One way to provide expandability is to dispose one or more reliefs into shaft 16. The relief may be any feature that provides expandability, such as slots 46, or slits. Alternatively, the shaft may be made of a thermoplastic material or other material or structure known in the art to resiliently expand, or it may include corrugated, expandable flex zones, or other expandable materials or structures that will be apparent to persons skilled in the art.

Looking particularly at FIGS. 13 and 14, as the distal end of shaft 12 is drawn completely into the distal end of shaft 16, displacement member 24 displaces ring 44 beyond the end of instrument 10 and around tissue 100 extending from recess 20.

Because shaft 16 has an equal or smaller OD than the largest OD of the distal, extendible portion 22 of inner shaft 12, Shaft 16 does not add thickness to the largest outer diameter of the instrument. In this way, the largest outer diameter of the insertable portion of instrument 10 depends on the thickness of the portion of shaft 12 that defines tissue-receiving recess 20. Since the outer shaft's thickness is not added into that outer diameter, it is possible to insert the instrument through smaller insertion channels than would otherwise be possible.

FIG. 6 shows a preferred embodiment of displacement member 24. In this embodiment, the distal end of outer shaft 12 comprising displacement member 24 is blunted to provide a broader surface to bear against ring 44. The blunt surface of displacement member 24 may be provided by, for example, folding inwardly the end of the tube forming shaft 16, or affixing a separate piece or pieces of material thereto. If the displacement member 24 is not sufficiently blunt, it may invert or damage the ring. The blunt surface helps prevent ring(s) 44 from inverting upon itself during the displacement procedure and from being damaged.

FIGS. 15–22 show another embodiment of the present invention. Except as noted below, instrument 110 is similar in construction and operation to instrument 10 of FIGS. 1–14. In instrument 110, the distal portion of the inner tube is not flared to have a larger OD than the inner diameter of the outer shaft. More specifically, instrument 110 comprises intermediate shaft 112 slideably disposed within outer shaft 116. Intermediate shaft 112 includes a ring retainer 114 disposed on a distal portion 122 of shaft 112 that is extendible from the distal end of outer shaft 116. Rings 44a and 44b may be disposed on ring retainer 114. Retainer 114 forms a region of reduced outer diameter in shaft 112. This area of reduced diameter may be preformed in shaft 112, or alternatively, the elastic tension of a ring 44 around retainer 114 may constrict shaft 112 to a reduced diameter by constructing the ring retainer of a flexible material, such as a thermoplastic or polyimide or other flexible material.

In this embodiment, the distal portion of outer shaft 116 need not be expandable as in instrument 10. Instead, ring retainer 114 on intermediate shaft 112 is expandable. One or more relief's 146 may be disposed in ring retainer 114 to allow expansion of retainer 114. The reliefs may be in the form of slits or slots in the material. Alternatively, reliefs could be omitted in favor of constructing the tube from a flexible polymer, for example, which is expandable. Other expandable structures and materials will be apparent to persons skilled in the art.

An inner shaft 115 comprising a hollow tube is slideably disposed within intermediate shaft 112. Inner shaft 115 is engageable with the tapered section of shaft 112 comprising retainer 114, as shaft 115 is slid distally relative to retainer 114. FIG. 15 shows inner tube 115 in an unadvanced proximal position with retainer 114 unexpanded. In this position, ring retainer 114 has a smaller diameter than adjacent proximal and distal segments of shaft 112.

The section of inner shaft 112 that is distal and adjacent to retainer 114 defines interior recess 120 for receiving tissue. In use, inner shaft 115 is advanced from a first position where the distal end of shaft 115 is proximal retainer 114. As inner shaft 115 is advanced through the interior of the section of shaft 112 comprising retainer 114, the larger diameter of shaft 115 causes the smaller diameter of the shaft forming retainer 114 to expand to have approximately the same outer diameter as the adjacent sections of shaft 112. Grasper 128 then may be extended from the distal end of the instrument to grasp tissue.

Next, the grasping assembly 126 may be retracted proximally to pull tissue into tissue receiving recess 120. The distal end of shaft 116 comprises displacement member 124. The displacement member 124 may be advanced distally relative to retainer 114 to displace one or more rings 44a and 44b disposed ring retainer 114 beyond the distal end of instrument 110 and around tissue extending from recess 120.

In the embodiment of FIGS. 15–22, outer shaft 116 has the largest OD of the tubular components, as labeled in FIG. 15. Grasping assembly 126, inner tube 115, and shaft 112 are sized to fit within outer shaft 116. As with other embodiments of this invention, this embodiment can be made small enough for insertion through channels as small as 5 mm or less. Smaller insertion channel diameters are possible because the rings are disposed around a necked-down, expandable area of reduced diameter on intermediate shaft 112. The OD of the instrument is principally limited by size of the tissue to be retracted.

The embodiment of FIG. 23 is similar to the embodiments of FIGS. 15–22. However, in this embodiment the section of the intermediate shaft distal to the ring retainer need not have a greater outer diameter than the diameter of the ring retainer. More specifically, FIG. 23 shows an intermediate shaft 212 slideably disposed in outer shaft 116. An inner tube 115 is slideably disposed within intermediate shaft 212. A grasper assembly with grasper 28 is slideably disposed within inner tube 115. The distal portion of shaft 212 comprises ring retainer 214. Ring retainer 214 is a section of shaft 212 having a smaller outer diameter than the adjacent proximal section of shaft 212. Section 240 of shaft 212 increases in diameter moving proximally from retainer 214.

In this embodiment, as the distal end of inner tube 115 moves forward, it encounters the distal end section of shaft 212 having a reduced diameter. This section of shaft 212 serves as ring retainer 214. As inner tube 115 advances through this section, it expands the ring retainer 214, in the same way as was described above for ring retainer 114 in instrument 110. The ring retainer 214 may also be constructed and operated in the same way as ring retainer 114. For example, reliefs 146 are also provided in retainer 214 to provide expandability.

When retainer 214 is expanded, grasping assembly 26 may be advanced through the interior passage defined by the ring retainer to extend grasper 28 from the distal end of the instrument. Grasper 28 may grasp tissue and retract it into the opening at the distal end inner tube 115. Displacement member 124, comprising the distal end of shaft 116, may then be advanced to contact ring 44 held on retainer 214. As described for the earlier discussed embodiments, displacement member 124 pushes ring 44 beyond the end of the instrument and around the tissue held by the instrument.

As an alternative to using inner shaft 115 to expand retainer 114 or 214, a grasping assembly could also serve the function of the inner tube if the distal portion of the grasper assembly has sufficient diameter and contact area to engage and expand the ring retainer. For example, looking at FIGS. 24–28 (described in more detail below) grasper 328 disposed on shaft 312 could provide an integral shaft unit containing grasper and expander functions. This shaft unit could be slideably disposed in shaft 212 in place of inner tube 115 and grasping assembly 26.

FIGS. 24–30 show another embodiment of a ligation instrument 310 according to this invention. In this embodiment, inner shaft 312 is slideably disposed in outer shaft 316. The distal portion 322 of shaft 312 is extendible from the distal end of shaft 316. The distal end of shaft 312 includes a tissue grasping assembly 326 comprising grasper 328, notch 330, and latch mechanism 47. The grasper 328 is in the form of a bullet-tipped hook. The latch mechanism 47 shown comprises a pivotal gate adapted to close over the opening of notch 330. The gate 47 has a free distal end and a proximal end pivotably affixed to shaft 312 at a location proximal to notch 330.

A ring retainer 314 is proximally adjacent grasping assembly 326 on shaft 312. The ring retainer comprises a tapered region of shaft 312. In operation, a distal portion of shaft 312 is extended from outer shaft 316. The instrument is manipulated to capture tissue in notch 330. As shaft 312 is retracted into tube 316, the distal end of tube 316 contacts latch mechanism 47 and urges the latch mechanism over the opening of notch 330 to keep tissue 100 from falling free of the notch as it is drawn into tissue receiving recess 320. At the same time, displacement member 324 contacts ring 44 urging it over the tissue extending from the end of the instrument.

FIG. 30 shows an alternative embodiment of a latch 347 comprising a collapsible cone 347 which closes over the opening of notch 330 as shaft 312 is retracted proximally into shaft 316. The collapsible cone 346 may be made, for example, from a thin, resilient plastic material, as shown in FIG. 30. Alternatively, it may be in the form of a synthetic woven material or a wire-form net, as generally shown in FIG. 34. It may be mechanically affixed, chemically welded, or glued around the shaft. The collar is affixed at its proximal border so that its opposite end is free and closeable over the opening of notch 330.

FIGS. 31–36 show alternatives to bullet-tip grasper 328. The grasper 428 in FIGS. 32a and 32b is in the form of a blade, which may be used to dissect, cut, or separate tissue. The blade may be sharpened to provide cutting edge that is straight, radiused, serrated, or blunted, for example. The grasper 528 of FIGS. 33a and 33b is in the form of a pointed tip, which may be used to pierce tissue. It may also take the form of generally a spherical tip with a suitably small radius, for example. Of course, combinations and variations of these tips are possible. For example, the piercing tip and blade could be combined into a single grasper. In addition, tissue grasping assembly 326, and its variations, could be combined with any of the earlier described embodiments instead of the forceps shown.

A further embodiment of a grasper is shown in FIGS. 35–36. Grasper 626 includes a channel 331 adapted to receive an elongate section of tissue, such as a section of fallopian tube to facilitate the capture of the tissue. The grasper may include multiple channels 331a and 331b. Preferably, the channel(s) is longitudinally disposed in the proximal, lateral surface of the grasper, as illustrated in the FIGS. 35–36.

Figure 3:
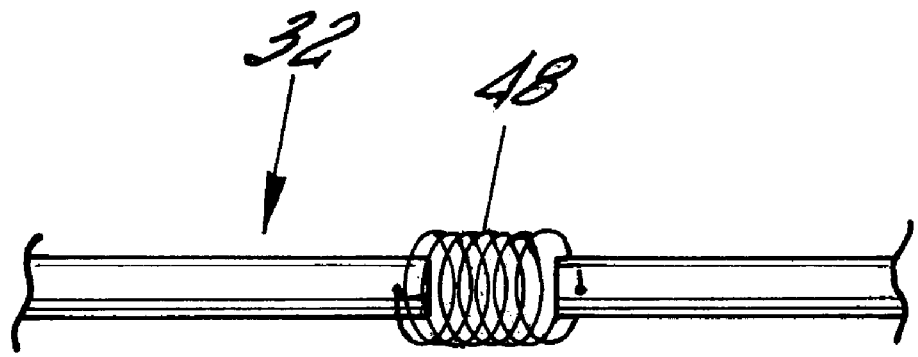
FIG. 3 shows one embodiment of a shaft of the present invention that includes a safety linkage in the form of a spring.

Any of the embodiments discussed herein may include a safety linkage to guard against a surgeon retracting a fallopian tube too forcefully into the recess of the instrument. The safety linkage prevents excessively forceful retraction to reduce the risk of damage to a Fallopian tube. An example safety linkage 48 is shown in FIGS. 3 and 4. In one embodiment, safety linkage comprises a spring between sections of connecting rod 32, as shown in FIG. 3. The spring acts as a damper: if there is too much resistance caused by retraction of a Fallopian, the spring stretch and limit the amount of force applied to the fallopian tube by the associated spring constant. The spring will maintain the reduced retractile force on the fallopian tube until it is eased within the inner diameter ("ID") of inner shaft 12. The spring may be incorporated between any two points of connecting rod 32. The linkage may also comprise a hydraulic or pneumatic shock mechanism which dampens retraction force on the tissue.

In another embodiment of the invention, safety linkage 48 comprises a magnetic link in connecting rod 32. In this link, magnets 150 and 152 are attached to adjacent end sections in rod 32. When the magnets are in contact with one another, the connecting rod 32 is one integral unit. A preferred magnet is made from neodymium metal. Should the surgeon try to pull the fallopian tube into the ID of the inner shaft too forcefully, the magnetic link breaks, stopping the advancement of the Fallopian tube, and helping to prevent damage to the organ. The physician may then move the connecting rod control out until the magnets reattached, and continue the procedure.

Other functions may also be optionally incorporated into the invention. The distal end of the instrument could include an electrosurgical tip for cutting or coagulating tissue in bipolar or monopolar mode. For example, the electrode could comprise the tip of grasper 28 or 328 or any other grasper described herein with the necessary coaxial or parallel electrical leads and insulation being disposed within, or on, the shaft of the grasper assembly 26. Aspiration and irrigation functions could also be incorporated into the instrument through tubes that are part of, added to, the instrument. For example, multiple lumens for fluid delivery or instrument access could be provided on the inside or outside of the instrument.

It is well known in the art how to actuate multiple concentric tubes relative to each other as seen, for example, in U.S. Pat. No. 4,226,239, which is hereby expressly incorporated by reference for its teachings on actuating concentrically disposed elements.

Referring to FIGS. 1–11, an example of an actuator assembly for instrument 10 is shown. Actuator assembly 50 includes housing 52, rotatable lever 54, spring 56, trigger tube 58. Elongate grip elements 62 and 64 extend from the body of housing 50 opposite each other. Grip element 62 is adapted to be gripped by the middle finger and the lower residing fingers. Grip element 64 is adapted to be gripped by the index finger, while the thumb inserts into the thumb ring 60.

Actuator assembly 50 includes a central bore (not shown) for receiving the assembly of inner shaft 12, outer shaft 16, and grasping assembly 26. A recess is disposed in the proximal end of assembly 50 which is adapted to receive a biasing element such as spring 56 and trigger tube 58. The proximal end of outer shaft 16 extends through the central bore and the bores of trigger tube 58 and spring 56. The proximal end of outer shaft 16 is attached to thumb ring 60.

Grasping assembly 26 is slideably disposed in inner shaft 12. A biasing element such as spring 68 is disposed against the proximal end of inner shaft 12 and the distal face of thumb ring 60. The assembly of inner shaft 12 and grasping assembly 26 is slideably disposed within outer shaft 16. Inner shaft 12 and outer shaft 16 each have proximal slots 13 and 15, respectively. These slots are aligned with each other for assembly in housing 52, and they define the relative travel of the shafts. Slot 15 provides travel for slot 13, as slot 13 moves relative to housing 52 The slots are further aligned with aperture 76 in housing 52 and slot 78 in trigger tube 58. Retainer 80, e.g., a pin or screw, is placed through aperture 76 and the aforementioned slots to secure connecting rod 32 in a stationary position relative to housing 52. The connecting rod 32 may include a socket 81 for receiving the retainer.

When thumb ring 60 is pulled backwards, it slides inner shaft 12 and grasping assembly 26 forward relative to outer shaft 16, as illustrated in FIG. 1*a*. As the proximal end of slot 13 in inner shaft 12 encounters retainer 80, it drags inner shaft 12 proximally relative to outer shaft 16, compressing spring 68. The proximal end of inner shaft 12 has limited rearward movement because housing 52 encounters the distal face of thumb ring 60. As a result, the grasper assembly extends forward of the distal opening of inner shaft 12. Tissue can be grasped and retracted by maneuvering grasper 28 so that the tissue is between the grasper's arms. Housing 52 is then moved backward, which moves inner shaft 12 over the arms of the grasper to enclose the arms and the tissue in recess 20, as illustrated in FIG. 1*b*. During tissue retraction, the instrument is moved forward to maintain the distal end of the instrument in about the same relative position in the patient's body. If the instrument is not maintained in the same relative position, there is a risk of damage to the tissue connected to the instrument.

The next step is ring displacement over the tissue. Trigger tube 58 is rotatably disposed in the bore of housing 52. The proximal portion of the central bore of housing 52 has a wider diameter than the distal portion to accommodate and seat spring 56. A proximal portion of trigger tube 58 is also disposed in this area of wider diameter, and extends a predetermined distance proximally from housing 52. A flange 66 is disposed on the proximal end of trigger tube 58. Accordingly, spring 56 biases cylinder 58 relative to housing 52, allowing coaxial displacement of the two components. The forward movement of cylinder 58 is limited by flange 66, which eventually blocks cylinder 58 from further forward movement.

The extended portion is fitted with rotatable lever 54 for rotating the trigger tube relative to housing 52. Slot 78 in trigger tube 58 is oriented in a generally transverse direction relative to the central bore of the housing 52. When cylinder 58 is rotated by lever 54 relative to housing 52, trigger tube 58 moves proximally or distally relative to housing 52 because of the transverse orientation of slot 78 relative to the central bore of housing 52. In other words, retainer 80 and slot 78 interact in a camming fashion.

Slot 78 includes at its opposite ends locking notches 72 and 74, oriented relatively perpendicular to slot 78. Retainer 80 may be slipped into these notches to lock cylinder 58 into a proximal or distal position. Thumb ring 60 compresses spring 56 into the proximal portion of housing 52's central bore. The degree of compression depends on the extent trigger tube 58 is proximally extended from housing 52. The distally most extended position is used to displace a first ring from the instrument. In the proximal position, a second ring can be displaced from the instrument. FIG. 1*c* represents instrument 10 after displacing a ring.

To be reusable, a medical instrument must be sterilizable. The present invention can include certain features to facilitate the disassembly of the instrument for cleaning. For example, relative to instrument 10, removing retainer 80 and thumb ring 60 allows the separation of the shafts and grasping assembly. Accordingly, the thumb ring 60 and proximal end of outer shaft 16 could include mated threads so that they may be screwed together. Retainer 80 may be in the form of a removable pin or screw. Preferably, housing 52 includes a means to retain the pin so it is not lost. The retention means could be a plastic string, metal chain, or other means to keep the pin from dislodging from the housing.

The various embodiments of the invention, the shafts may be made from known materials for use in medical devices. For example, the shafts could be constructed using stainless steel or other substantially rigid materials such as thermoplastics, nitinol, and other materials that meet the functional objectives of the invention.

Placement of an elastic ring on the ring retainer of the invention may be facilitated if the shaft holding the ring retainer is immobilized relative to the other shafts in the instrument. Accordingly, a locking means 84 may be provided to fix the shafts during the loading of a ring. The locking means may be in the form of a spring biased pin which can be depressed through aligned apertures in inner 12 and outer shaft 16. When the button is seated in the aperture, the shafts are locked into the relative positions shown in FIG. 9. In this locked position, an elastic ring may be loaded onto the ring retainer This specification is not intended to limit the scope of this invention but to illustrate novel examples of it. Other embodiments are contemplated by the inventors. Aspects of some of the foregoing embodiments may be combined with aspects of other embodiments to create additional embodiments. Persons skilled in the art will recognize that these and other variations and modifications are possible that do not depart from the scope and teachings of this specification.

What is claimed is:

1. An instrument for ligation of tissue comprising:
    a first shaft having a distal portion and a proximal portion;
    a second shaft slideably disposed in the first shaft;
    a tissue receiving recess at the distal end of the instrument;
    a grasper slideably disposed in the first shaft and adapted to extend from the instrument to grasp and retract tissue into the tissue receiving recess;
    a ring retainer for receiving at least one elastic ring, the ring retainer comprising a distal segment of the second shaft, the ring retainer having reduced diameter relative to an adjacent second segment of the second shaft; and
    a displacement member disposed on the distal end of the first shaft for pushing a ring off the ring retainer and around tissue extending from the tissue receiving recess.

2. The instrument of claim 1 wherein at least one of the ring retainer and the distal portion of the first shaft are expandable radially, the expansion allowing the slideable displacement member disposed on the distal end of the first shaft to push a ring off the ring retainer and around tissue extending out of the tissue receiving recess.

3. The instrument of claim 1 wherein the grasper is slideably disposed in the second shaft.

4. The instrument of claim 2 wherein the tissue receiving recess is disposed in a distal portion of the second shaft extendible from the first shaft, said extendible portion including a generally funnel-shaped section of tubing, with the ring retainer being disposed on the neck of the funnel.

5. The instrument of claim 2 wherein the distal portion of the first shaft is expandable radially.

6. The instrument of claim 5 wherein at least one relief slot is included in the expandable portion of the first shaft to facilitate its expansion.

7. The instrument of claim 2 wherein the ring retainer is expandable radially.

8. The instrument of claim 7 further comprising an inner tube slideably disposed in the second shaft for expanding the ring retainer.

9. The instrument of claim 7 wherein the ring retainer includes at least one relief slot to facilitate its expansion.

10. The instrument of claim 2 wherein the distal portion of the second shaft has a flared region of greater diameter than the distal end of the first shaft so as to expand the distal portion of the first shaft when the second shaft is pulled therein.

11. The instrument of claim 1 wherein the tissue receiving recess is in the distal end of the first shaft.

12. The instrument of claim 1 wherein the tissue receiving recess is in the distal end of the second shaft.

13. The instrument of claim 1 wherein the grasper is disposed on the distal end of the second shaft.

14. The instrument of claim 13 wherein the grasper comprises a notch disposed in the distal end of the second shaft, the notch being adapted to capture and retract tissue within the tissue receiving recess, and the ring retainer being located on a portion of the second shaft proximal the notch.

15. The instrument of claim 14 further wherein the distal end of the second shaft is adapted to cut or pierce tissue.

16. The instrument of claim 14 further comprising a latching mechanism disposed on the second shaft proximal the notch, the latching mechanism being closeable over the opening of the notch.

17. The instrument of claim 14 wherein the latch is engageable with the distal end of the first shaft to latch over the notch during retraction of tissue into the first shaft.

18. The instrument of claim 14 wherein the distal end includes a channel adapted to receive a section of fallopian tube during retraction of the tube into the tissue receiving recess.

19. The instrument of claim 1 wherein the distal end of the first shaft comprises the displacement member.

20. The instrument of claim 1 wherein the displacement member comprises a blunted distal end of the first shaft for pushing a ring from the ring retainer.

21. The instrument of claim 1 wherein the grasper comprises forceps.

22. The instrument of claim 1 further comprising a safety linkage disposed proximal to the grasper for preventing overly forcefully retraction of tissue into the tissue receiving recess.

23. The instrument of claim 1 further comprising a means for locking the first shaft relative to the second shaft.

24. An instrument for ligation comprising:
    a ring retainer located proximally to a tissue receiving recess, the tissue receiving recess being disposed in the end of an elongate element;
    a grasper for retracting tissue within the tissue receiving recess disposed proximal the recess and extendible therefrom;
    a displacement member slideably disposed proximal to the ring retainer and adapted to displace a ring placed on the ring retainer off the ring retainer and around tissue extending from the tissue receiving recess, the displacement member being radially expandable over the exterior surface defining the tissue receiving recess.

25. An instrument for ligation comprising:
    a ring retainer located proximal to a tissue receiving recess, the tissue receiving recess disposed in the end of an elongate element;
    a grasper for retracting tissue within the tissue receiving recess disposed proximal to the recess and extendible therefrom;
    the ring retainer being expandable from a first unexpanded condition to a second, radially expanded condition, a displacement member being slideably disposed on the instrument so that it may displace a ring held on the ring retainer in the second expanded condition around tissue extending from the tissue receiving recess.

26. An instrument for ligation of tissue comprising:

an outer shaft having a distal portion and a proximal portion;

an inner shaft slideably disposed in the outer shaft;

a tissue receiving recess at the distal end of the inner shaft;

a grasper slideably disposed in the inner shaft and adapted to extend from the instrument to grasp and retract tissue into the tissue receiving recess;

a ring retainer for receiving at least one elastic ring, the ring retainer comprising a first distal segment of the inner shaft, the ring retainer having reduced diameter relative to an adjacent second more distal second segment of the inner shaft;

the outer shaft being adapted to expand to receive the second segment of the inner shaft; and a displacement member disposed on the distal end of the outer shaft for pushing a ring off the ring retainer and around tissue extending from the tissue receiving recess.

27. The instrument of claim 26 further comprising a means for locking the outer shaft relative to the inner shaft.

28. An instrument for ligation of tissue comprising:

an outer shaft having a distal portion and a proximal portion;

an intermediate shaft slideably disposed in the outer shaft;

a tissue receiving recess at the distal end of the intermediate shaft;

a grasper slideably disposed in the inner shaft adapted to extend from the instrument to grasp and retract tissue into the tissue receiving recess;

a ring retainer for receiving at least one elastic ring, the ring retainer comprising a distal segment of the intermediate shaft having reduced diameter relative to an adjacent distal segment of the intermediate shaft, the ring retainer being radially expandable;

an inner shaft slideably disposed in the intermediate shaft for expandably engaging the ring retainer; and a displacement member disposed on the distal end of the outer shaft for pushing a ring off the ring retainer and around tissue extending from the tissue receiving recess.

29. The instrument of claim 28 further comprising a means for locking the outer shaft shaft relative to the intermediate shaft.

30. An instrument for ligation of tissue comprising:

an outer shaft having a distal portion and a proximal portion;

an inner shaft slideably disposed in the outer shaft;

a tissue receiving recess at the distal end of the outer shaft;

a grasper slideably disposed on the end of the inner shaft and adapted to extend from the instrument to grasp and retract tissue into the tissue receiving recess;

a ring retainer for receiving at least one elastic ring, the ring retainer comprising a first distal segment of the inner shaft, the ring retainer disposed adjacent a second more distal second segment of the inner shaft, the second segment comprising the grasper; and a displacement member disposed on the distal end of the outer shaft for pushing a ring off the ring retainer and around tissue extending from the tissue receiving recess.

31. The instrument of claim 30 further comprising a means for locking the outer shaft relative to the inner shaft.

* * * * *